United States Patent [19]

Fahmy et al.

[11] 4,262,015

[45] Apr. 14, 1981

[54] N-ALKYLTHIO- AND N-ARYLTHIOSULFINYLCARBAMATE ESTERS

[75] Inventors: Mohamed A. H. Fahmy; Tetsuo R. Fukuto, both of Riverside, Calif.

[73] Assignee: The Regents of the University of California, Los Angeles, Calif.

[21] Appl. No.: 18,417

[22] Filed: Mar. 7, 1979

[51] Int. Cl.$^3$ ................. C07D 317/44; C07C 149/43; C07C 125/04; C07D 307/77
[52] U.S. Cl. ............................. 424/282; 260/340.5 R; 260/340.9 R; 260/346.22; 260/464; 260/465 D; 260/465.4; 424/285; 424/300; 560/10; 560/16; 560/17; 560/134; 560/135; 560/136; 560/137; 560/148
[58] Field of Search .................. 560/148, 16, 17, 134, 560/135, 136, 137; 424/300, 282, 285; 260/340.5 R, 346.22, 464, 465 D, 465.4

[56] References Cited

U.S. PATENT DOCUMENTS

| | | | |
|---|---|---|---|
| 3,663,594 | 5/1972 | Brown et al. | 560/10 |
| 3,843,689 | 10/1974 | Brown et al. | 560/135 |
| 3,914,259 | 10/1975 | Brown et al. | 560/136 |
| 3,950,374 | 4/1976 | Ueda et al. | 424/300 |
| 3,969,407 | 7/1976 | Phillips et al. | 260/465 D |
| 4,122,204 | 10/1978 | D'Silva | 560/16 |
| 4,138,423 | 2/1979 | D'Silva | 260/464 |

FOREIGN PATENT DOCUMENTS

| | | | |
|---|---|---|---|
| 1095806 | 6/1961 | Fed. Rep. of Germany | 560/137 |
| 49-25132 | 6/1974 | Japan | 424/300 |

Primary Examiner—Ethel G. Love
Attorney, Agent, or Firm—Herzig & Walsh, Inc.

[57] ABSTRACT

A novel class of chemical compounds useful as pesticides consists of N-alkylthio- and N-arylthiosulfinylcarbamate esters. The preparation of these compounds and their formulation to control insects are exemplified.

40 Claims, No Drawings

N-ALKYLTHIO- AND N-ARYLTHIOSULFINYLCARBAMATE ESTERS

BACKGROUND OF THE INVENTION

This invention relates to the general field of pesticides, and is particularly concerned with the production of insecticides for the control of both household insects and crop insects.

U.S. Pat. No. 3,997,549 to Fukuto and Black discloses N-arylsulfenylated derivatives of benzofuranyl methylcarbamates as effective pesticides.

U.S. Pat. No. 4,006,231 to Black and Fukuto discloses N-aminosulfenylated derivatives of carbofuran as effective pesticides.

U.S. Pat. No. 3,843,689 to Brown discloses production of N-methyl- or N-phenyldithiocarbamates produced from N-chlorothiocarbamates, as insecticides.

The object of the present invention is to provide another novel class of carbamates which are effective pesticides, and procedure for preparing same.

SUMMARY OF THE INVENTION

The novel carbamate ester compounds of the invention are generally N-alkylthio- and N-arylthiosulfinylcarbamate esters. The compounds are prepared by reacting an N-chlorosulfinylcarbamate ester with an alkylmercaptan or arylthiol, in a suitable organic solvent in the presence of a hydrogen chloride acceptor such as pyridine.

The resulting compounds of the invention are highly effective against certain pests and insects, and have substantially reduced mammalian toxicity, e.g. as compared to other potent insecticides such as carbofuran, described in U.S. Pat. No. 3,474,171. Thus, the invention compounds, while having high toxicity toward certain pests or insects, are relatively safe to mammals.

DETAILED DESCRIPTION OF THE INVENTION AND PREFERRED EMBODIMENTS

The sulfinylcarbamate esters or compounds of the invention have the formula noted below:

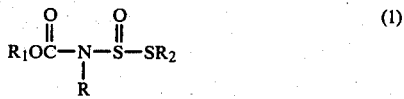

(1)

wherein R is a hydrocarbyl (hydrocarbon) group containing only hydrogen and carbon, either aliphatic or aromatic; preferably a straight chain, branched or carbocyclic (five or six membered ring) alkyl, phenylalkyl or phenyl, and containing from 1 to 12 carbon atoms, and further exemplified hereinafter.

$R_1$ can be a hydrocarbyl group containing only hydrogen and carbon, and from 1 to 20 carbon atoms, either aliphatic or aromatic, including substituted or unsubstituted alkyl, cycloalkyl, phenylalkyl and naphthylalkyl; and substituted or unsubstituted aryl, such as phenyl and naphthyl; and wherein the aforementiond groups can be substituted with one or more halogen, cyano, nitro, alkyl, alkylthio and alkoxy groups; a 5 or 6 membered heterocyclic ring containing O or S atoms, e.g. benzothienyl, furanyl, benzofuranyl and 1,3-benzodioxolyl; or the $>C=N-$ group. The $>C=N-$ group can be represented more specifically by the formula:

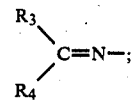

where
$R_3$ is hydrogen, alkyl, alkylthio or cyano, and
$R_4$ is alkyl, alkylthio, alkoxy, alkanoyl, alkoxycarbonyl, dialkylaminocarbonyl or phenyl, all of which can be unsubstituted or substituted with one or more cyano, nitro, alkylthio, alkylsulfinyl, alkylsulfonyl or alkoxy groups.

Where $R_1$ is aryl, preferred examples of such aryl groups are as follows:

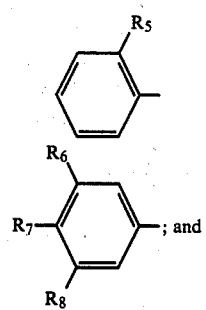

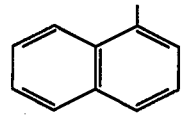

where
$R_5$ is hydrogen, alkoxy, alkylthio, alkyl, alkylthioalkyl, 2-dioxolanyl or halogen, e.g. Cl or Br;
$R_6$ is alkyl, alkoxy, alkoxyalkyl or halogen;
$R_7$ is hydrogen, alkyl, halogen, alkylthio, alkoxy, dialkylamino or formyl(alkyl)amino;
$R_8$ is hydrogen or alkyl:
and wherein the number of aliphatic carbon atoms in $R_3$, $R_4$, $R_5$, $R_6$, $R_7$, and $R_8$, individually should not exceed eight:
$R_2$ can be a hydrocarbyl group, e.g. substituted or unsubstituted alkyl, cycloalkyl, phenylalkyl, naphthylalkyl, and wherein the permissible substituents on said groups are one or more halogen, cyano, nitro, dialkylamino, alkyl, alkylthio or alkoxy groups; or $R_2$ can be aryl, e.g. phenyl or naphthyl, unsubstituted or substituted in any position by one or more alkyl, cycloalkyl, alkylthio, alkoxy, or halogen groups; and $R_2$ contains 1 to 20 carbon atoms.

Thus, the invention broadly is directed to carbamates according to formula (1) above wherein R is a hydrocarbyl group containing from 1 to 12 carbon atoms; $R_1$ is selected from the group consisting of a hydrocarbyl group containing from 1 to 20 carbon atoms, a 5 to 6 membered heterocyclic ring containing 0 or S atoms, and the $>C=N-$ group and $R_2$ is a hydrocarbyl group containing from 1 to 20 carbon atoms.

Preferred carbamates of the invention are those of formula (1) above, where R is a hydrocarbyl group containing from 1 to 12 carbon atoms; $R_1$ is selected from the class consisting of hydrocarbyl groups containing from 1 to 12 carbon atoms, heterocyclic rings containing O or S atoms, and containing 5 to 6 members in the heterocyclic nucleus, and a group containing the >C=N— radical; and $R_2$ is a hydrocarbyl group containing from 1 to 12 carbon atoms.

Thus, in one group of preferred carbamate ester compounds of the invention, $R_1$ is a hydrocarbyl group containing from 1 to 12 carbon atoms, either aliphatic or aromatic, including alkyl, e.g. methyl, ethyl, isopropyl, propyl, isobutyl, cycloalkyl, e.g. cyclohexyl, phenylalkyl, naphthylalkyl; aryl, e.g. phenyl, naphthyl, alkylphenyl, e.g. tolyl, xylyl, alkylnaphthyl, any of which can contain substituents such as halogen, e.g. chlorine or bromine, alkoxy, alkylthio and dialkylamino, and R is alkyl, phenyl, phenylalkyl and naphthylalkyl groups, as exemplified above, containing 1–12 carbon atoms. Particularly preferred are those compounds where $R_1$ is alkyl, phenyl, alkylphenyl and naphthyl groups, and which can be unsubstituted or substituted, e.g. with halogen, alkoxy, dialkylamino groups, and the like, and especially wherein $R_1$ is 3-alkylphenyl such as 3-isopropyl- and 3-sec-butylphenyl, 2-alkoxyphenyl such as 2-isopropoxyphenyl or 1-naphthyl. Particularly preferred also is the group of carbamate esters wherein $R_1$ is a heterocyclic ring, and including fused-on heterocyclic rings, containing one or two O or S atoms, and 5 to 6 members in the heterocyclic nucleus, e.g. benzofuranyl or 1,3-benzodioxolyl, and especially a 2,3-dihydrobenzofuranyl-7 group having the formula (2) below, and the 1,3-benzodioxol-4 group having the formula (3) below:

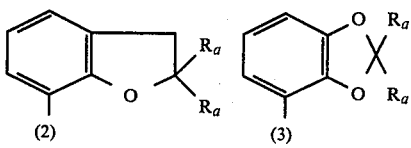

(2)     (3)

where $R_1$ is an alkyl group of 1 to about 4 carbon atoms, e.g. methyl, ethyl, propyl, n-butyl, and both $R_a$'s can be the same or different, and most preferably wherein $R_1$ is the 2,3-dihydro-2,2-dimethylbenzofuranyl-7 group or the 2,2-dimethyl-1,3-benzodioxol-4 group; and R is alkyl. Another particularly preferred class of carbamates of the invention are those wherein $R_1$ is a group containing the >C=N— radical, as defined above, and R is alkyl. Such >C=N— groups can be, for example, the following:

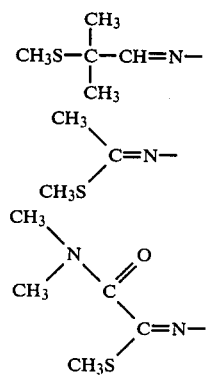

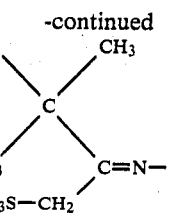

$R_2$ in all of the above preferred compounds is a hydrocarbyl group preferably alkyl or aryl. Such groups can be substituted by alkyl, alkoxy, alkylthio, halogen, such as chlorine or bromine, nitro, cyano and the like. Among the preferred alkyl groups are methyl, ethyl, propyl, isopropyl, n-butyl, tert.-butyl, with increasing carbon atoms up to dodecyl. Among the preferred aryl groups are substituted phenyl. Especially preferred substituents are alkyl, cyano, and halogen groups in one or more positions in the phenyl ring, such as 2-tolyl, 4-tolyl, 2,4-xylyl, 4-tert.-butylphenyl, 4-chlorophenyl, 4-cyanophenyl, and the like.

The N-alkylthio- and N-arylthiosulfinylcarbamate esters of the invention can be prepared by the following general reaction scheme:

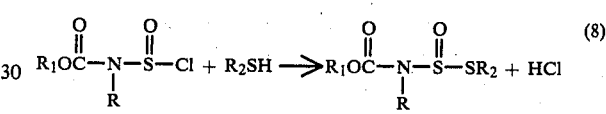

where R, $R_1$, and $R_2$ are defined above. The N-chlorosulfinylcarbamate ester intermediate is formed by the reaction of the corresponding carbamate with thionyl chloride, preferably using pyridine as hydrogen chloride acceptor in an inactive polar solvent such as tetrahydrofuran. Non-polar solvents such as hexane also may be used. Such ester can be formed in high yield using essentially equivalent quantities of the carbamate and thionyl chloride and slightly more than an equivalent amount of pyridine. These novel intermediates are described in the copending application Ser. No. 18,416, filed Mar. 7, 1979, by M. A. H. Fahmy and T. R. Fukuto.

Without isolation, the N-chlorosulfinylcarbamate ester intermediates can react in situ with alkylmercaptans or arylthiols in the presence of pyridine in slight excess to equivalent amounts as a hydrogen chloride acceptor. Generally the reaction of alkylmercaptans and arylthiols with chlorosulfinylcarbamates is carried out at temperatures from 0° to 20° C. However, hindered thiols can be reacted up to room temperature or higher, depending upon the reactivity of the chlorosulfinylcarbamate. In general, lowering the temperature during the addition of thiols results in higher yield of products.

It will be understood that if desired, the N-chlorosulfinylcarbamate ester starting material in reaction (8) above can be initially prepared and isolated as an intermediate compound, and such compound then reacted with the appropriate $R_2SH$ compound, as noted in the above reaction scheme.

The following are examples of preparation of the carbamate ester compounds of the invention.

EXAMPLE I

Synthesis of 2,3-dihydro-2,2-dimethylbenzofuranyl-7 (methyl)(n-butylthiosulfinyl)carbamate.

To a solution of 4.4 g (0.02 mol) 2,3-dihydro-2,2-dimethylbenzofuranyl-7 methylcarbamate in 20 ml dry tetrahydrofuran was added 1.9 g (0.024 mol) pyridine followed by 2.5 g (0.021 mol) thionyl chloride. The mixture was stirred at room temperature for 4 hours. Pyridine (1.9 g, 0.024 mol) was added and the mixture was cooled in an ice-water bath. To this stirring solution was added, dropwise, 1-butanethiol (1.8 g, 0.02 mol) in 2 ml tetrahydrofuran. After the complete addition of the thiol, the mixture was allowed to warm up to room temperature and kept at this temperature for ½ hour. Ether, 150 ml, was added to the mixture and washed four times (25 ml each) with water. The ether solution was dried over anhydrous sodium sulfate and the solvent was evaporated under vacuum. The residue was subjected to high vacuum (0.1 mm) for several hours. Nmr spectrum of this crude product showed a complete conversion of 2,3-dihydro-2,2-dimethylbenzofuranyl-7 methylcarbamate to its butylthiosulfinyl derivative. An analytical sample was obtained by preparative thin-layer chromatography.

Analysis calculated for $C_{16}H_{23}NO_4S_2$; carbon, 53.75%; hydrogen, 6.48%. Found: carbon, 53.97%; hydrogen 6.48%.

EXAMPLE II

Synthesis of 2,3-dihydro-2,2-dimethylbenzofuranyl-7 (methyl)(t-butylthiosulfinyl)carbamate.

To a solution of 4.4 g 2,3-dihydro-2,2-dimethylbenzofuranyl-7 methylcarbamate (0.02 mol) in 20 ml anhydrous tetrahydrofuran, was added 1.9 g pyridine (0.024 mol) and 2.5 g thionyl chloride (0.021 mol). The mixture was stirred at room temperature for 4 hours. Then pyridine (1.9 g, 0.024 mol) was added to the stirring mixture followed by t-butylmercaptan (1.8 g, 0.02 mol) added dropwise. The temperature of the reaction mixture was maintained at about 18°–20° C., using a water bath, during the addition of the mercaptan. The reaction mixture was stirred for an additional one hour at room temperature. Ether (150 ml) was added, and workup and purification were similar to Example 1. Nmr spectrum of the oily crude product showed better than 90% conversion of the carbamate to its t-butylthiosulfinyl derivative.

Analysis calculated for $C_{16}H_{23}NO_4S_2$; carbon, 53.75%; hydrogen, 6.48%. Found: carbon, 54.12%; hydrogen, 6.51%.

EXAMPLE III

Synthesis of 2,3-dihydro-2,2-dimethylbenzofuranyl-7 (methyl)(phenylthiosulfinyl)carbamate.

To a solution of 4.4 g 2,3-dihydro-2,2-dimethylbenzofuranyl-7 methylcarbamate (0.02 mol) in 20 ml dry tetrahydrofuran, was added 1.9 g pyridine (0.024 mol) and 2.5 g thionyl chloride (0.021 mol). The mixture was stirred at room temperature for 4 hours. The mixture was cooled in an ice-water bath and 1.9 g pyridine (0.024 mol) was added. Benzenethiol (2.2 g, 0.02 mol) was added dropwise with stirring. The temperature was allowed to rise up to room temperature and stirring was continued for an additional 15 minutes. Ether (150 ml) was added and the mixture was worked up as described in Example 1, resulting in an oily residue. A sample of this product was purified further by thin-layer chromatography, and the NMR spectrum obtained.

Analysis calculated for $C_{18}H_{19}NO_4S_2$; carbon, 57.27%; hydrogen, 5.07%. Found: carbon, 57.70%; hydrogen 4.76%.

EXAMPLE IV

Synthesis of 2,3-dihydro-2,2-dimethylbenzofuranyl-7 (methyl)(4-t-butylphenylthiosulfinyl)carbamate.

To a solution of 2,3-dihydro-2,2-dimethylbenzofuranyl-7 methylcarbamate (4.4 g, 0.02 mol), and pyridine (1.9 g, 0.024 mol) in 20 ml dry tetrahydrofuran, was added 2.5 g thionyl chloride (0.021 mol), and stirred at room temperature for 4 hours. Pyridine (1.9 g, 0.024 mol) was added and followed by 4-t-butylbenzenethiol (3.5 g, 0.021 mol) added dropwise at room temperature. Stirring was continued for an additional one hour and the mixture was worked up similar to Example I.

Analysis calculated for $C_{22}H_{27}NO_4S_2$; carbon, 60.94%; hydrogen, 6.28%. Found: carbon, 61.31%; hydrogen, 6.08%.

EXAMPLE V

Synthesis of 2,3-dihydro-2,2-dimethylbenzofuranyl-7 (methyl)(2-methyl-4-t-butylphenylthiosulfinyl)carbamate.

To a solution of 4.4 g 2,3-dihydro-2,2-dimethylbenzofuranyl-7 methylcarbamate (0.02 mol) in 20 ml dry tetrahydrofuran was added 1.9 g pyridine (0.024 mol) and 2.5 g thionyl chloride (0.021 mol). The mixture was stirred for 4 hours at room temperature. Pyridine (1.9 g, 0.024 mol) was added and followed by 2-methyl-4-t-butylbenzenethiol (3.6 g, 0.02 mol), added dropwise while cooling with an ice-water bath. The temperature was allowed to rise to room temperature and stirring was continued for an additional one hour. Workup was carried out similar to Example I, and the oily product was purified by thin-layer chromatography.

Analysis calculated for $C_{23}H_{29}NO_4S_2$; carbon, 61.72%; hydrogen, 6.53%. Found: carbon, 61.97%; hydrogen, 6.74%.

EXAMPLE VI

Synthesis of 2-isopropoxyphenyl (methyl)(n-butylthiosulfinyl)carbamate.

To a solution of 4.2 g 2-isopropoxyphenyl methylcarbamate (0.02 mol) in 20 ml dry tetrahydrofuran was added 1.9 g pyridine (0.024 mol), and 2.5 g thionyl chloride (0.021 mol). The mixture was stirred for 4 hours at room temperature. Pyridine (1.9 g, 0.024 mol) was added, followed by 1.8 g 1-butanethiol (0.02 mol) added dropwise, while cooling the mixture in an ice-water bath. The temperature was allowed to rise to room temperature, and stirring was continued for an additional one hour. Workup and purification of product was similar to procedure described in Example I.

Analysis calculated for $C_{15}H_{23}NO_4S_2$; carbon, 52.14%; hydrogen, 6.71%. Found: carbon, 52.80%; hydrogen, 6.79%.

EXAMPLE VII

Synthesis of 2-isopropoxyphenyl (methyl)(2-methyl-4-t-butylphenylthiosulfinyl)carbamate.

To a solution of 4.2 g 2-isopropoxyphenyl methylcarbamate (0.02 mol) in 20 ml dry tetrahydrofuran was added 1.9 g pyridine (0.024 mol), and 2.5 g thionyl chloride (0.021 mol). The mixture was stirred for 4 hours at room temperature. Pyridine (1.9 g, 0.024 mol) was added and followed by 2-methyl-4-t-butylbenzenethiol (3.6 g, 0.02 mol), added dropwise at water bath temperature. The mixture was stirred for an additional one hour at room temperature, and worked up in a manner similar to Example I. A sample of the oily product was purified further by preparative thin-layer chromatography, and the NMR spectrum obtained.

Analysis calculated for $C_{22}H_{29}NO_4S_2$: carbon, 60.66%; hydrogen, 6.71%. Found: carbon, 61.15%; hydrogen, 6.71%.

EXAMPLE VIII

Synthesis of S-methyl N-[N'-methyl-N'-t-butylthiosulfinylcarbamoyloxy]thioacetimidate.

A mixture of 3.3 g S-methyl N-[N'-methylcarbamoyloxy]thioacetimidate (0.02 mol), 1.9 g pyridine (0.024 mol), and 2.5 g thionyl chloride (0.021 mol), in 20 ml dry tetrahydrofuran was stirred at room temperature for 4 hours. Pyridine (1.9 g, 0.024 mol) was added and followed by 1.8 g t-butylmercaptan (0.02 mol) added dropwise at water bath temperature. Stirring was continued for an additional one hour, and methylene chloride (150 ml) was added. The mixture was washed several times with water and the organic layer was dried over anhydrous sodium sulfate. After solvent evaporation the residue was crystallized from ether yielding 4.1 g of product m.p. 51°–53° C.

Analysis calculated for $C_9H_{18}N_2O_3S_3$: carbon, 36.22%; hydrogen, 6.08%. Found: carbon, 36.80%; hydrogen, 6.29%.

EXAMPLE IX

Synthesis of S-methyl N-[N'-methyl-N'-phenylthiosulfinylcarbamoyloxy]thioacetimidate.

A mixture of 3.3 g S-methyl N-[N'-methylcarbamoyloxy]thioacetimidate (0.02 mol), 1.9 g pyridine (0.024 mol) and 2.5 g thionyl chloride (0.021 mol), in 20 ml dry tetrahydrofuran was stirred at room temperature for 4 hours. Pyridine (1.9 g, 0.024 mol) was added and followed by 2.2 g benzenethiol (0.02 mol) added dropwise at water bath temperature. Stirring was continued for an additional hour, and the mixture was worked up as described for Example I. The resulting oily residue was purified by preparative thin-layer chromatography, and the NMR spectrum obtained.

Nmr spectrum of the product in chloroform-d-TMS showed the following absorptions: δ 7.8–7.25 (m, 5H, aromatic protons), 3.25 (s, 3H, $NCH_3$), 2.4 (s, 3H, $N=CCH_3$), 2.25 (s, 3H, $SCH_3$).

EXAMPLE X

Synthesis of 3-isopropylphenyl (methyl)(t-butylthiosulfinyl)carbamate.

To a solution of 4.0 g 3-isopropylphenyl methylcarbamate in 20 ml dry tetrahydrofuran was added 1.9 g pyridine (0.024 mol) and 2.5 g thionyl chloride (0.021 mol). The mixture was stirred at room temperature for 6 hours. Pyridine (1.9 g, 0.024 mol) was added and followed by 1.8 g t-butylmercaptan (0.02 mol) added dropwise at water bath temperature. The mixture was stirred for an additional hour at room temperature and 150 ml ether was added. Workup and purification were carried out as described in Example I.

Analysis calculated for $C_{15}H_{23}NO_3S_2$: carbon, 54.68%; hydrogen, 7.04%. Found: carbon, 54.55%; hydrogen, 6.83%.

EXAMPLE XI

Synthesis of 3-isopropylphenyl (methyl)(2-methyl-4-t-butylphenylthiosulfinyl)carbamate.

To a solution of 4.0 g 3-isopropylphenyl methylcarbamate in 20 ml dry tetrahydrofuran was added 1.9 g pyridine (0.024 mol) and 2.5 g thionyl chloride (0.021 mol). The mixture was stirred at room temperature for 6 hours. Pyridine (1.9 g, 0.024 mol) was added and followed by 3.6 g of 2-methyl-4-t-butylbenzenethiol (0.02 mol) added dropwise at room temperature. The mixture was stirred for an additional hour and 150 ml ether was added. The mixture was worked up similar to other examples and a sample of the oily product was purified by thin-layer chromatography.

Analysis calculated for $C_{22}H_{29}NO_3S_2$: carbon, 62.97%; hydrogen, 6.97%. Found: carbon, 63.40%; hydrogen, 6.89%.

EXAMPLE XII

Synthesis of 2-methyl-2-(methylthio)propionaldehyde O-[(methyl)(dodecylthiosulfinyl)carbamoyl]oxime.

To a solution of 2-methyl-2-(methylthio)propionaldehyde O-(methylcarbamoyl)oxime (3.8 g, 0.02 mol) in 20 ml dry tetrahydrofuran was added 1.9 g pyridine (0.024 mol) and 2.5 g thionyl chloride (0.021 mol). The mixture was stirred for 6 hours at 18°–20° C. Pyridine (1.9 g, 0.024 mol) was added and followed by 4.4 g 1-dodecanethiol (0.022 mol) added dropwise at ice-water bath temperature. The product was worked up similar to other examples and a sample was further purified by preparative thin-layer chromatography.

Analysis calculated for $C_{19}H_{38}N_2O_3S_3$: carbon, 52.01%; hydrogen, 8.73%. Found: carbon, 52.59%; hydrogen, 9.01%.

EXAMPLE XIII

Synthesis of 1-naphthyl (methyl)(t-butylthiosulfinyl)carbamate.

To a solution of 1-naphthyl methylcarbamate (4.0 g, 0.02 mol) in 20 ml dry tetrahydrofuran was added 1.9 g pyridine (0.024 mol), and 2.5 g thionyl chloride (0.021 mol). The mixture was stirred at room temperature for 6 hours. The reaction mixture was cooled by the aid of an ice-water bath and 1.9 g pyridine (0.024 mol) was added followed by 1.8 g t-butylmercaptan (0.02 mol), added dropwise. After the complete addition of the mercaptan, the temperature was allowed to rise up to room temperature and the mixture was stirred for an additional 1 hour. Workup and purification were carried out as described in Example I.

Analysis calculated for $C_{16}H_{19}NO_3S_2$: carbon, 56.95%; hydrogen, 5.68%. Found: carbon, 57.51%; hydrogen, 6.82%.

EXAMPLE XIV

Synthesis of 1-naphthyl (methyl)(phenylthiosulfinyl)carbamate.

To a solution of 1-naphthyl methylcarbamate (4.0 g, 0.02 mol) in 20 ml dry tetrahydrofuran was added 1.9 g pyridine (0.024 mol) and 2.5 g thionyl chloride (0.021 mol). The mixture was stirred at room temperature for 6 hours. The reaction mixture was cooled in an ice-water bath and 1.9 g pyridine was added followed by 2.2 g benzenethiol (0.02 mol) added dropwise. Stirring was continued for an additional 1 hour and the mixture was worked up in the usual manner as previously described in Example I. A sample was purified by preparative thin-layer chromatography. Nmr spectrum of the pure product in chloroform-d-TMS showed the following absorptions: δ 8.1–6.9 (m, 12H, aromatic protons), 3.2 (s, 3H, $NCH_3$).

The following are additional examples of the sulfinyl carbamate compounds of the invention:

n-Propyl(tert.-butylthiosulfinyl)(ethyl)carbamate
iso-Propyl(tert.-butylthiosulfinyl)(methyl)carbamate
iso-Propyl(tert.-butylthiosulfinyl)(phenyl)carbamate
2,3-Dihydro-2,2-dimethylbenzofuranyl-7(4-bromophenylthiosulfinyl)(methyl)carbamate
2,2-Dimethyl-1,3-benzodioxolyl-4(n-butylthiosulfinyl)-(methyl)carbamate
S-Methyl N-[(4-tert.-butylphenylthiosulfinyl)(methyl)-carbamoyloxy]thioacetimidate
S-Methyl N-[(dodecylthiosulfinyl)(methyl)carbamoyloxy]-thioacetimidate
S-Methyl N',N'-dimethyl-N-(n-butylthiosulfinyl) (methyl)-carbamoyloxy-1-thio-oximidate
S-Methyl N',N'-dimethyl-N-(tert.-butylthiosulfinyl)-(methyl)carbamoyloxy-1-thio-oximidate
2-Chlorophenyl(ethylthiosulfinyl)(methyl)carbamate
3-sec.-Butylphenyl(ethylthiosulfinyl)(methyl)carbamate
2,2-Dimethyl-1,3-benzodioxolyl-4(ethylthiosulfinyl)-(methyl)-carbamate The insecticidal N-alkylthio- and N-arylthiosulfinyl-carbamate esters of the invention may be formulated with the usual carriers including additives and extenders used in the preparation of insecticidal compositions. Thus, the toxicants of this invention like most insecticidal agents, are generally not applied full strength, but are incorporated with the adjuvants and carriers normally employed for facilitating the dispersion of active ingredients, recognizing the accepted fact that the formulation and mode of application of a toxicant may affect the activity of the material.

The present compounds may be made into liquid concentrates by solution of emulsification in suitable liquids such as organic solvents, and into solid concentrates by admixing with talc, clays, and other known solid carriers used in the insecticide art. These concentrates are compositions containing about 5–50% toxicant and the rest inert material which includes dispersing agents, emulsifying agents, and wetting agents. The concentrates are diluted for practical application, with water or other liquid for liquid sprays or with additional solid carrier for application as a dust or granular formulation.

The concentration of the toxicant in the dilution generally used for application is normally in the range of about 2% to about 0.001%. Many variations of spraying and dusting compositions in the art may be used, by substituting a compound of this invention into compositions known or apparent to the art.

Insecticidal compositions may be formulated and applied with other active ingredients, including other insecticides, nematicides, acaricides, fungicides, plant regulators, fertilizers, etc. In applying the chemicals, it is obvious that an effective amount and concentration of the carbamate ester compounds of the invention should be employed.

BIOLOGICAL ACTIVITY

Representative compounds of the N-arylthio- and N-alkylthiosulfinylcarbamate esters of the invention were tested for insecticidal activity against two insect species, house flies, Musca domestica, and mosquito larvae, Culex pipiens. Stock 1% concentrated solutions of each of the test compounds were made in acetone, and such solutions diluted with acetone to a concentration of 0.001–0.1%. House flies were treated topically on the notum by 1 μl of each of the diluted acetone solutions and percent mortality was counted 24 hours after application. Insects were held at a constant temperature of 60° F. Larvicidal activity was determined by applying 1 ml of the acetone solution in 100 ml of water containing 20 3rd instar mosquito larvae. Results are presented as $LD_{50}$ in μg/g for house flies and $LC_{50}$ in ppm for mosquito larvae.

Mammalian toxicity was determined against Swiss white mice. The test compound was applied orally using corn oil as the carrier. Results are given as $LD_{50}$ in mg of compound per kg body weight. The toxicological data for a number of typical N-arylthio- and N-alkylthiosulfinylcarbamates of the invention are summarized in Table I.

The term "$LD_{50}$" represents the dose needed to kill 50% of the test animals, and the term "$LC_{50}$" is the concentration needed to kill 50% of the mosquito larvae. In interpreting the values in the table below, the lower the value for $LD_{50}$ for house flies and for $LC_{50}$ for mosquito larvae, the greater the insecticidal potency or toxicity of that particular compound. On the other hand, the higher the value of $LD_{50}$ for mice, the lower the mammalian toxicity or the greater is the mammalian safety of such compound.

| Compound of Example | House flies $LD_{50}$ (μg/g) | Culex $LC_{50}$ (ppm) | Mice $LD_{50}$ (mg/kg) |
|---|---|---|---|
| I | 16.5 | | 45 |
| II | 9 | 0.01 | 70 |
| III | 7 | .05 | 32 |
| IV | 11.8 | | 92 |
| V | 8.8 | | 70 |
| VI | 31 | | 1050 |
| VII | 27 | | >1000 |
| X | 75 | | 250 |
| XI | 62.5 | | 450 |
| IX | 6.5 | | 150 |
| VIII | 5.5 | | 135 |
| XII | 12 | | |
| XIII | 235 | | >1000 |
| XIV | 350 | | >1000 |

The relatively low values for the various compounds of the invention listed in Table I for $LD_{50}$ for house flies and $LC_{50}$ for mosquito larvae (Culex) indicates high toxicity of the invention compounds as against such insects. Thus, for example the parent material of the compounds of Examples I to V of Table I, carbofuran, which is 2,3-dihydro-2,2-dimethyl-7-benzofuranyl methylcarbamate, has an $LD_{50}$ value for house flies, of about 6.5. The $LD_{50}$ values for house flies of the related invention compounds of Examples I through V, are comparable, ranging from 7 to 16, thus showing comparable insecticidal toxicity of such invention compounds to the potent insecticide carbofuran. However, and of particular significance, the mammalian toxicity of the invention compounds of Examples I to V of Table I above, as indicated by their high $LD_{50}$ values ranging from 32 to 92 for mice, is low, as compared to the much higher toxicity as indicated by an $LD_{50}$ value of from about 2 to about 8, found for the parent carbamate ester insecticide, carbofuran. It is also noted that the $LD_{50}$ value of 1050 for the compound of Example VI is much higher than the $LD_{50}$ value of 60 found for the parent carbamate ester compound, which is the carbamate starting material in Example VI, and the $LD_{50}$ value of 250 for the compound of Example X is substantially higher than the $LD_{50}$ value of 16 found for the parent carbamate ester compound, which is the carbamate starting material of Example X. Thus, the above Table shows that the N-alkylthio- and N-arylthiosulfinylcarbamate esters of the invention have high insecticidal activity or potency, but have substantially reduced mammalian toxicity or substantially greater mammalian safety.

While we have described particular embodiments of the invention for purposes of illustration, it will be understood that various changes and modifications within the spirit of the invention can be made, and the invention is not to be taken as limited except by the scope of the appended claims.

What is claimed is:

1. Carbamates having pesticidal activity of the formula:

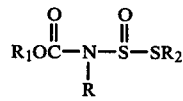

wherein R is a hydrocarbyl group containing from 1 to 12 carbon atoms; $R_1$ is selected from the group consisting of a hydrocarbyl group containing from 1 to 20 carbon atoms, a 5 to 6 membered heterocyclic ring consisting essentially of one to two O or S atoms, the remaining ring atoms being carbon atoms, and the group

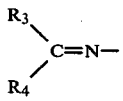

where $R_3$ is hydrogen, alkyl, alkylthio or cyano, and $R_4$ is alkyl, alkylthio, alkoxy, alkanoyl, alkoxycarbonyl, dialkylaminocarbonyl, or phenyl, which can be unsubstituted or substituted with cyano, nitro, alkylthio, alkylsulfinyl, alkylsulfonyl or alkoxy groups, the number of aliphatic carbon atoms in $R_3$ and $R_4$ not exceeding eight; and $R_2$ is a hydrocarbyl group containing from 1 to 20 carbon atoms.

2. Carbamates as defined in claim 1, wherein $R_1$ is an aryl group selected from the class consisting of:

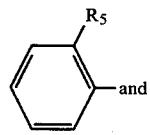

-continued

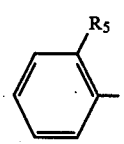

where
$R_5$ is hydrogen, alkoxy, alkylthio, alkyl, alkylthioalkyl, 2-dioxolanyl, or halogen;
$R_6$ is alkyl, alkoxy, alkoxyalkyl, or halogen;
$R_7$ is hydrogen, alkyl, halogen, alkylthio, alkoxy, dialkylamino or formyl(alkyl)amino; and
$R_8$ is hydrogen or alkyl; the number of aliphatic carbon atoms in $R_5$, $R_6$, $R_7$, and $R_8$, individually, not exceeding eight.

3. Carbamates as defined in claim 2, wherein $R_1$ is:

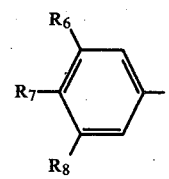

4. Carbamates as defined in claim 2, wherein $R_1$ is:

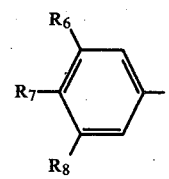

5. Carbamates as defined in claim 1, wherein $R_1$ is 1-naphthyl.

6. Carbamates as defined in claim 1, where $R_1$ is a 5 to 6 membered heterocyclic ring containing one to two O or S atoms, the remaining ring atoms being carbon atoms.

7. Carbamates as defined in claim 1, wherein $R_2$ is substituted or unsubstituted alkyl, cycloalkyl, phenylalkyl, naphthylalkyl, and wherein said groups can be substituted by one or more halogen, cyano, nitro, dialkylamino, alkyl, alkylthio, or alkoxy groups; phenyl or naphthyl unsubstituted or substituted by one or more alkyl, cycloalkyl, alkylthio, alkoxy, or halogen groups.

8. Carbamates as defined in claim 1, wherein R and $R_2$ are each alkyl.

9. Carbamates as defined in claim 1, wherein R is alkyl and $R_2$ is aryl.

10. Carbamates having pesticidal activity of the formula

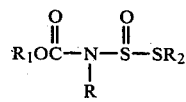

where R is a hydrocarbyl group containing from 1 to 12 carbon atoms; $R_1$ is selected from the class consisting of hydrocarbyl groups containing from 1 to 12 carbon atoms, heterocyclic rings consisting essentially of one to two O or S atoms, and containing 5 to 6 members in the heterocyclic nucleus, the remaining ring atoms being carbon atoms, and groups containing the group

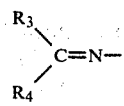

where $R_3$ is hydrogen, alkyl, alkylthio or cyano, and $R_4$ is alkyl, alkylthio, alkoxy, alkanoyl, alkoxycarbonyl, dialkylaminocarbonyl, or phenyl, which can be unsubstituted or substituted with cyano, nitro, alkylthio, alkylsulfinyl, alkylsulfonyl or alkoxy groups, the number of aliphatic carbon atoms in $R_3$ and $R_4$ not exceeding eight; and $R_2$ is a hydrocarbyl group containing from 1 to 12 carbon atoms.

11. Carbamates as defined in claim 10, wherein R is selected from the group consisting of alkyl, phenyl, phenylalkyl and naphthylalkyl.

12. Carbamates as defined in claim 10, wherein $R_2$ is selected from the group consisting of alkyl, phenyl and alkylphenyl.

13. Carbamates as defined in claim 10, wherein $R_1$ and R are each hydrocarbyl groups containing from 1 to 12 carbon atoms, and $R_2$ is selected from the group consisting of alkyl, phenyl, and alkylphenyl.

14. Carbamates as defined in claim 13, wherein $R_1$ and R are selected from the group consisting of alkyl, phenyl, alkylphenyl and naphthyl, and R is selected from the group consisting of alkyl, phenyl, phenylalkyl and naphthylalkyl.

15. Carbamates as defined in claim 10, wherein $R_1$ is selected from the group consisting of 3-isopropylphenyl, 3-sec.-butylphenyl, 2-isopropoxyphenyl and 1-naphthyl.

16. Carbamates as defined in claim 10, wherein $R_1$ is a heterocyclic ring containing one to two O or S atoms, and 5 to 6 members in the heterocyclic nucleus, the remaining ring atoms being carbon atoms.

17. Carbamates as defined in claim 16, wherein R is alkyl, and $R_2$ is selected from the group consisting of alkyl, phenyl, and alkylphenyl.

18. Carbamates as defined in claim 16, wherein $R_1$ is a benzofuranyl or a 1,3-benzodioxylyl group.

19. Carbamates as defined in claim 18, wherein R is alkyl and $R_2$ is selected from the group consisting of alkyl, phenyl and alkylphenyl.

20. Carbamates as defined in claim 10, wherein $R_1$ is selected from the class having the formulae:

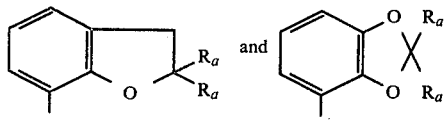

where $R_a$ is an alkyl group of 1 to about 4 carbon atoms, and both $R_a$'s can be the same or different, R is alkyl, and $R_2$ is selected from the group consisting of alkyl, phenyl and alkylphenyl.

21. Carbamates as defined in claim 10, wherein $R_1$ is the 2,3-dihydro-2,2-dimethylbenzofuranyl-7 group, or the 2,2-dimethyl-1,3-benzodioxol-4 group, R is alkyl and $R_2$ is selected from the group consisting of alkyl, phenyl, and alkylphenyl.

22. Carbamates as defined in claim 21, wherein R is methyl.

23. Carbamates of the formula

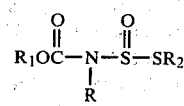

where R is a hydrocarbyl group containing from 1 to 12 carbon atoms; $R_1$ is selected from the class having the formulae:

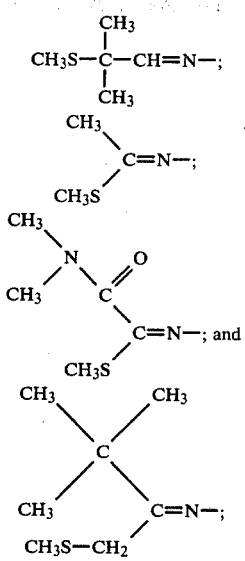

and $R_2$ is a hydrocarbyl group containing from 1 to 12 carbon atoms.

24. Carbamates as defined in claim 23, wherein R is alkyl and $R_2$ is selected from the group consisting of alkyl, phenyl, and alkylphenyl.

25. Carbamates as defined in claim 24, wherein R is methyl.

26. Carbamates as defined in claim 24, wherein $R_1$ is the group having the formula

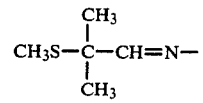

and R is methyl.

27. Carbamate as defined in claim 1, which is 2,3-dihydro-2,2-dimethylbenzofuranyl-7(methyl)(phenylthiosulfinyl)carbamate.

28. Carbamate as defined in claim 1, which is 2-isopropoxyphenyl(methyl)(n-butylthiosulfinyl)carbamate.

29. S-methyl N-[N'-methyl-N'-t-butylthiosulfinylcarbamoyloxy]thioacetimidate.

30. Carbamate as defined in claim 1, which is 3-isopropylphenyl(methyl)(2-methyl-4-t-butylphenylthiosulfinyl)carbamate.

31. Carbamate as defined in claim 1, which is 1-naphthyl(methyl)(t-butylthiosulfinyl)carbamate.

32. An insecticidal composition comprising an insecticidally effective amount of a carbamate as defined in claim 1, in admixture with a carrier.

33. An insecticidal composition comprising an insecticidally effective amount of a carbamate as defined in claim 10, in admixture with a carrier.

34. An insecticidal composition comprising an insecticidally effective amount of a carbamate as defined in claim 20, in admixture with a carrier.

35. An insecticidal composition comprising an insecticidally effective amount of a carbamate as defined in claim 23, in admixture with a carrier.

36. An insecticidal composition comprising an insecticidally effective amount of a carbamate as defined in claim 24, in admixture with a carrier.

37. The method of controlling insects which comprises applying to the sites of infestation an insecticidally effective amount of a compound as defined in claim 1.

38. The method of controlling insects which comprises applying to the sites of infestation an insecticidally effective amount of a compound as defined in claim 10.

39. The method of controlling insects which comprises applying to the sites of infestation an insecticidally effective amount of a compound as defined in claim 22.

40. The method of controlling insects which comprises applying to the sites of infestation an insecticidally effective amount of a compound as defined in claim 25.

* * * * *